United States Patent [19]

Ambrosius et al.

[11] Patent Number: 5,618,927
[45] Date of Patent: Apr. 8, 1997

[54] PROCESS FOR THE REACTIVATION OF DENATURED PROTEIN

[75] Inventors: Dorothea Ambrosius, Iffeldorf; Rainer Rudolph, Weilheim, both of Germany

[73] Assignee: Boehringer Mannheim GmbH, Mannheim-Waldhof, Germany

[21] Appl. No.: 867,679

[22] PCT Filed: Nov. 21, 1991

[86] PCT No.: PCT/EP91/02190

§ 371 Date: Jul. 2, 1992

§ 102(e) Date: Jul. 2, 1992

[87] PCT Pub. No.: WO92/09622

PCT Pub. Date: Jun. 11, 1992

[30] Foreign Application Priority Data

Nov. 22, 1990 [DE] Germany .................... 40 37 196.4

[51] Int. Cl.$^6$ .................................................. C07K 1/02
[52] U.S. Cl. .................... 530/412; 530/427; 530/402; 530/404; 530/405; 530/406; 530/408; 530/409; 530/410; 530/418; 530/422
[58] Field of Search ................... 530/412, 427, 530/402–406, 408–410, 418, 422

[56] References Cited

U.S. PATENT DOCUMENTS

| 4,933,434 | 6/1990 | Rudolph et al. | 530/405 |
| 5,077,392 | 12/1991 | Rudolph et al. | 530/402 |

OTHER PUBLICATIONS

Goding et al, 1988 Monoclonal . . . Practice, pp. 109–110.
Kabat et al., Experimental Immunochemistry, 1961, pp. 42–43.
Lohman et al., J Biol Chem., 1989, 264: 10139.

*Primary Examiner*—Frank C. Eisenschenk
*Attorney, Agent, or Firm*—Felfe & Lynch

[57] ABSTRACT

The invention concerns a process for the reactivation of denatured protein, in which the protein is incubated with a solution of Tris base or/and a salt of Tris at a concentration of at least 400 mmol/l and at a pH at which the protein to be treated can take up its native conformation.

12 Claims, No Drawings

PROCESS FOR THE REACTIVATION OF DENATURED PROTEIN

CROSS REFERENCE TO RELATED APPLICATIONS

This application is a continuation of PCT/EP91/02190, filed Nov. 21, 1991.

DESCRIPTION

The present invention concerns an improved process for the solubilization and renaturation of denatured protein wherein the protein is treated with a Tris buffer which has a concentration of at least 400 mmol/l of Tris base or of a Tris salt.

When proteins are produced in prokaryotic cells such as *E. coli*, difficultly soluble proteins aggregates (inclusion bodies) are often formed. Solubilization and renaturation steps are necessary in order to convert these proteins into their active form. The solubilization of proteins is a known process (see e.g. EP 0 361 475 A1, EP-A 0 114 506, EP-A 0 093 619 and EP-A 0 253 823).

In addition buffers as well as processes for the renaturation of denaturated proteins are known (see e.g. WO 87/02674, EP-A 0 364 926, EP 0 241 022).

An important factor in the reactivation of proteins (with or without disulphide bridges) which limits the yield of renatured protein is the competition between conversion of the denatured protein into the correct folding intermediate and the aggregation of several protein molecules. For this reason the concentration of denatured protein in the renaturation buffer is an important parameter for the yield of the renaturation process i.e. increasing concentrations of denatured protein promote aggregation and lower the relative yield of renatured protein with the conformation of the native protein.

In all processes known at present for the reactivation of proteins it is therefore necessary that the amount of denatured protein in the reaction mixture does not exceed a critical concentration. Since the protein is often only sparingly soluble in the reactivation buffer used, this therefore results in considerable disadvantages regarding lower yield, large amount of time needed and/or larger buffer volumes.

An object of the present invention is therefore to provide conditions for the reactivation of denatured proteins (i.e. in particular for the solubilization and renaturation), and to provide a buffer by which means the solubility of the denatured and renatured protein is substantially increased in comparison to known buffers.

This object is achieved according to the present invention by a process for the reactivation of denatured protein which is characterized in that the protein is incubated with a solution of Tris(hydroxymethyl)aminomethane base (denoted Tris in the following) disclosure or a salt of Tris at a concentration of at least 400 mmol/l and at a pH value at which the protein to be treated can take up its native conformation.

The use of a buffer which contains Tris base or salts of Tris at a concentration of more than 400 mmol/l for the reactivation of denatured proteins considerably increases the solubility of the renaturing proteins. This leads to a substantial increase in the yield of active protein in comparison to known standard methods. Although previously known reactivation buffers often contain Tris at a concentration of 50 to 100 mmol/l in order to buffer the reaction solution, the surprising property to mediate solubilization (and thus the ability to improve the renaturation yield) of Tris at a concentration of at least 400 mmol/l has previously not been recognized.

A salt of Tris within the meaning of the present invention is understood as a Tris salt of an arbitrary organic or inorganic acid. Examples of Tris salts are for instance Tris acetate, Tris benzoate, Tris borate, Tris carbonate, Tris citrate, Tris-HCl, Tris maleate, Tris nitrate, Tris oxalate, Tris phosphate, Tris succinate, Tris sulphate and suchlike.

The process according to the present invention is suitable for the general renaturation of proteins whereby the cause of the denaturation (salt, heat etc.) is not in fact critical. Although the process according to the present invention is preferably suitable for the renaturation of products produced by genetic engineering and which occur in an inactive form as inclusion body material, the process can, however, in principle also be applied to other denatured proteins. In particular the process according to the present invention is applicable to the processes disclosed in WO 87/02673, EP-A 0 241 022 and EP-A 0 364 926. In this connection WO 87/02673 discloses a process for the activation of non-glycosylated tPA after expression in prokaryotes by cell lysis, solubilization under denaturing and reducing conditions and reactivation under oxidizing conditions in the presence of GSH/GSSG, in which a pH value of 9 to 12, a GSH concentration of 0.1 to 20 mmol/l, a GSSG concentration of 0.01 to 3 mmol/l and a non-denaturing concentration of a denaturing agent are used in the reactivation step. EP-A 0 241 022 discloses a process for the renaturation of denatured proteins in solution in a renaturation buffer in which a solution of the protein to be renatured is prepared at the critical concentration in the chosen buffer and, after formation of the folding intermediate, further protein to be renatured is added in an amount necessary to achieve the critical concentration. EP-A 0 364 926 concerns a process for the activation of biologically active proteins produced by genetic engineering and expressed in prokaryotes after cell lysis by solubilization under denaturing and reducing conditions and subsequent reactivation under oxidizing and renaturing conditions in which a protein concentration of 1–1000 μg/ml is used and dialysis is carried out between solubilization and reactivation against a buffer which has a pH value between 1 and 4, and contains 4 to 8 mol/l guanidine hydrochloride or 6 to 10 mol/l urea.

The process according to the present invention can be carried out in one of two ways. One variant is to work with a Tris buffer of the stated concentration so that Tris or/and a Tris salt is also used for adjusting the pH. The second variant is to work with a buffer which has previously been described for the corresponding process and to additionally add Tris or/and a salt of Tris. This means that the pH value of the incubation solution is adjusted by a buffer substance which is different from Tris. In both cases it is expedient to take care that the addition of Tris or the increase in Tris concentration does not result in a change in pH.

The incubation is carried out at a pH value at which the protein to be treated can exist in a native conformation. This means that the incubation in the process according to the present invention does not take place at a pH value which does not allow the formation of a native protein conformation. Native protein conformations are in turn understood to include such secondary, tertiary and, if desired, quarternary structures in which the protein can have biological activity.

The process according to the present invention comprises the incubation of a denatured protein with a Tris solution which has a concentration of at least 400 mmol/l. The Tris concentration is preferably 0.4 to 2 mol/l, particularly preferably about 1 mol/l Tris. With some proteins (e.g. with antibody fragments) optimal reactivation yields are already achieved at Tris concentrations in the range of 0.5 mol/l.

The yield of a renaturation process depends, as already described above, on the concentration of the protein in the renaturation solution. For the process according to the present invention a protein concentration is preferably chosen which is in the range up to 4000 μg/ml. Depending on the type of protein and the renaturation process, protein concentrations exceeding this range can, however, also prove to be suitable.

In the process according to the present invention the denatured protein is either added continuously or batchwise (e.g. pulse renaturation) to the renaturation solution. In many cases (e.g. in the renaturation of tPA and tPA derivatives) it has also proven to be advantageous to add 0.2 to 1 mol/l arginine to the incubation solution.

Preferred examples of proteins which can be renatured by the process according to the present invention are recombinant tPA or tPA muteins (in particular a non-glycosylated tPA mutein having the domain composition K2P), recombinant granulocyte colony stimulating factor (G-CSF) or antibodies or their fragments. The process according to the present invention is, however, not limited to these examples but rather can be applied to any protein.

The advantages of the reactivation process according to the present invention include, in particular, an increase in the final yield of active protein of 30 to 300% compared to a process in which a buffer is used which has a lower Tris concentration. Moreover, the concentration of denatured protein in the renaturation buffer can be increased without losses in the final yield i.e. the renaturation process becomes substantially quicker and more effective.

In particular the process according to the present invention is advantageous for pulse renaturation in a renaturation reactor. In this case the yield of renatured protein is increased and in addition the protein concentration per pulse can be increased, which results in a shortening of the reactivation period. It is also possible to pulse up to a higher final protein concentration in the renaturation preparation without observing a reduction in the renaturation yield. As a consequence the buffer volume is considerably reduced. A pulse renaturation procedure that has proven to be particularly advantageous is one in which the renaturation is carried out in a buffer containing arginine and a Tris concentration of about 1 mol/l where the concentration of the protein to be renatured is increased by about 200 μg/ml per pulse.

It is intended to further elucidate the invention by the following examples.

| | Abbreviations: |
|---|---|
| GSH | reduced glutathione |
| GSSG | oxidized glutathione |
| tPA | tissue plasminogen activator |
| $C_{prot}$ | protein concentration |
| Arg | arginine |
| Gdn | guanidine |
| renat. | renaturation |
| CK | creatine kinase |

EXAMPLE 1

Dependence of the renaturation yield on the incubation time up to the addition of the second pulse (+/−1 mol/l Tris)

Starting Material:

Inclusion bodies (IB's) of the tPA mutein K2P were produced according to WO 90/09437 (Example 1) and subsequently solubilized according to EP-A 0 361 475 A1 (Example 1) and converted into the mixed disulphide. In examples 2 to 5 the starting material was used in an analogous manner.

| Renaturation: | 0.6 mol/l arginine/HCl, pH 8.5 |
|---|---|
| | 1 mmol/l EDTA |
| | 0.7 mmol/l reduced glutathionine (GSH) |
| | +/− 1 mol/l Tris |
| | $C_{prot.}$ = 140 μg/ml per pulse |
| Addition of 2nd pulse: | 1 to 9 h (see table) |
| Incubation: | 12 h at room temperature after addition of the last pulse. |

TABLE 1

| Time 2nd pulse (h) | WITHOUT TRIS Activity (+fibrin) (U/ml) | 1 MOL/L TRIS Activity (+fibrin) (U/ml) |
|---|---|---|
| 0 | 2855 | 4736 |
| 1 | 4671 | 9256 |
| 2 | 4974 | 9732 |
| 3 | 5060 | 10359 |
| 4 | 5233 | 9343 |
| 5 | 5168 | 9645 |
| 6 | 6845 | 10185 |
| 7 | 6152 | 9252 |
| 8 | 6814 | 10726 |
| 9 | 7115 | 10335 |

The determination of the activity of the renatured tPA mutein K2P and the definition of the unit U are described by Lill, (ZGIMAL 42 (1987), 478–486).

It can be seen in Table 1 that in arginine buffer without Tris the maximum renaturation yield is achieved when the residence time is >6 h before adding the second pulse. If 1 mol/l Tris is added to the reaction mixture then the following changes take place: the maximum yield in the renaturation is increased by 30–40%; denatured protein can be added even after a residence time of 1 to 3 h without a reduction in the renaturation yield.

EXAMPLE 2

Renaturation: Dependence on the Tris concentration and the Arg/guanidine ratio

Starting Material:

Inclusion bodies (IB's) of the tPA mutein K2P produced as described in Example 1.

| | Renaturation: |
|---|---|
| | Experiment A: dependence on Tris |
| Tris: | 0.6 mol/l arginine/HCl, pH 8.5 |
| | 1 mmol/l EDTA |
| | 0.7 mmol/l GSH |
| | 0, 50, 100, 500, 1000 and 2000 mmol/l |
| | $C_{prot.}$ = 80 μg/ml |
| Incubation: | 24 h at room temperature |
| | Experiment B: buffer dependence |
| Buffer: (1) | 1 mmol/l EDTA, pH 8.5 |
| | 0.7 mmol/l GSH |
| | $C_{prot.}$ = 80 μg/ml |
| | 0.6 mol/l arginine/HCl |

-continued

| | Renaturation: | |
|---|---|---|
| (2) | 0.4 mol/l arginine/HCl plus 0.2 mol/l guanidine (Gdn)/HCl | |
| (3) | 0.2 mol/l arginine/HCl plus 0.5 mol/l guanidine (Gdn)/HCl +/−1 mol/l Tris in each case | |
| Incubation: | 24 h at room temperature | |

TABLE 2A

Experiment A: dependence on Tris

| Tris (mmol/l) | Activity (+fibrin) (U/ml) |
|---|---|
| 0 | 2173 |
| 50 | 2750 |
| 100 | 2651 |
| 500 | 3902 |
| 1000 | 5339 |
| 2000 | 5131 |

TABLE 2B

Experiment B: variation of the buffer

| Buffer | Additives | Activity (+fibrin) (U/ml) |
|---|---|---|
| (1) 0.6 mol/l Arg | — | 2047 |
|  | 1 mol/l Tris | 3553 |
| (2) 0.4 mol/l Arg/ 0.2 mol/l Gdn | — | 1577 |
|  | 1 mol/l Tris | 4350 |
| (3) 0.2 mol/l Arg/ 0.5 mol/l Gdn | — | 1402 |
|  | 1 mol/l Tris | 3277 |

Experiment A: The yield increases with an increase in the Tris concentration in the renaturation buffer. The optimum for the renaturation is at a Tris concentration of ca. 1 mol/l. Surprisingly the renaturation yield increases between 100 mmol/l and 500 mmol/l Tris. Experiment B: The yield is substantially increased (factor 2 to 3) in all cases by addition of 1 mol/l Tris.

EXAMPLE 3

Dependence of the renaturation on the protein concentration (+/−1 mol/l Tris)

Starting Material:

Inclusion bodies (IB's) of the tPA mutein K2P produced according to Example 1.

| Renaturation: | Buffer A: 0.6 mol/l Arg/HCl, pH 8.5 1 mmol/l EDTA 0.7 mmol/l GSH |
|---|---|
| $C_{prot.}$: | 112, 223 and 446 µg/ml |
| | Buffer B: 0.6 mol/Arg/HCl, pH 8.5 1 mol/l Tris 1 mmol/l EDTA 0.7 mmol/l GSH |
| $C_{prot.}$: | 112, 223, 446, 893, 2230 and 4460 µg/ml |
| Incubation: | 24 h at room temperature |

The result of this experiment is shown in the following Table 3.

TABLE 3

| Tris (mol/l) | $C_{prot.}$ (µg/ml) | Activity (+fibrin) (U/ml) | Activity/$C_{prot.}$ (U/mg) |
|---|---|---|---|
| 0 | 112 | 2875 | 25670 |
|  | 223 | 4187 | 18780 |
|  | 446 | 5956 | 13350 |
| 1 | 112 | 2900 | 25890 |
|  | 223 | 5171 | 23190 |
|  | 446 | 10163 | 22790 |
|  | 893 | 13286 | 14880 |
|  | 2230 | 17483 | 7840 |
|  | 4460 | 24930 | 5590 |

The renaturation rate decreases with increasing protein concentrations in the arginine buffer without Tris. If 1 mol/l Tris is added to the buffer then no significant decrease in the renaturation yield (activity/$C_{prot.}$) can be measured up to a protein concentration of 400 µg/ml. Only at higher protein concentrations is there a decrease in the yield with increasing concentrations.

EXAMPLE 4

Pulse renaturation: +/−1 mol/l Tris

Starting Material:

Inclusion bodies (IB's) of the tPA mutein K2P, produced according to Example 1.

| Renaturation: | 0.6 mol/l Arg/HCl, pH 8.5 1 mmol/l EDTA 0.7 mmol/l GSH Tris: +/− 1 mol/l $C_{prot.}$ = 150 µg/ml per pulse residence time: 12 h final concentration: 1500 µg/ml the mixed disulphides are kept at 0° C. reaction under nitrogen |
|---|---|

The result of this experiment is shown in the following Table 4.

TABLE 4

| Tris (mol/l) | $C_{prot.}$ (µg/ml) | Activity (+fibrin) (U/ml) | Activity/$C_{prot.}$ (U/mg) |
|---|---|---|---|
| 0 | 150 | 3000 | 20000 |
|  | 450 | — | |
|  | 750 | 11622 | 15496 |
|  | 1050 | 14430 | 13743 |
|  | 1350 | 17507 | 12968 |
| 1 | 150 | 4353 | 29020 |
|  | 450 | 10978 | 24395 |
|  | 750 | 17319 | 23092 |
|  | 1050 | 22600 | 21524 |
|  | 1350 | 27920 | 20681 |

A significant increase in turbidity occurs at protein concentrations of 700 µg/ml when pulsing without Tris, whereas the pulse with the addition of 1 mol/l Tris is completely clear even at a protein concentration of 1.5 mg/ml. The final yield was increased by ca. 30% by the addition of 1 mol/l Tris.

EXAMPLE 5

Pulse renaturation: approximation to a continuous process (+/−1 mol/l Tris)

Starting material:

Inclusion bodies (IB's) of the tPA mutein K2P, produced according to Example 1.

| Renaturation: | 0.6 mol/l Arg/HCl, pH 8.5 |
|---|---|
| | 0.7 mmol/l GSH |
| | 1 mmol/l EDTA |
| | +/− 1 mol/l Tris |
| | pulse: residence time: 30 min. |
| | $C_{prot.}$ -increase per pulse: (A) 9.3 µg/ml; (B) 31 µg/ml |
| | pumping period: 2 min. |
| | final concentration: 3000 µg/ml |
| | the mixed disulphides are kept at 0° C., reaction under $N_2$ |

The result of this experiment is shown in Table 5.

TABLE 5A

| Time (h) | $C_{prot.}$ (µg/ml) | Activity (+fibrin) (U/ml) | Activity/$C_{prot.}$ (U/mg) |
|---|---|---|---|
| 1 mol/l Tris, $C_{prot.}$ = 9.3 µg/ml per 30 min. | | | |
| 16 | 245 | 10223 | 41726 |
| 23 | 527 | 23295 | 44203 |
| 42 | 800 | 30405 | 38006 |
| 48 | 904 | 43339 | 47941 |
| 69 | 1299 | 43964 | 33844 |
| 73 | 1375 | 49505 | 36003 |
| 137 | 2580 | 107499 | 41666 |
| 146 | 2759 | 104009 | 37698 |
| without Tris, $C_{prot.}$ = 9.3 µg/ml per 30 min. | | | |
| 8 | 114 | 2932 | 25719 |
| 24 | 338 | 5635 | 16671 |
| 40 | 563 | 14723 | 26150 |
| 56 | 788 | 24035 | 30501 |
| 72 | 1013 | 27909 | 27550 |
| 88 | 1238 | 33802 | 27303 |
| 104 | 1463 | 37734 | 25792 |
| 120 | 1688 | 46420 | 27500 |
| 176 | 2485 | 59195 | 23821 |
| 192 | 2710 | 62098 | 22914 |
| 208 | 2935 | 61764 | 21044 |
| 224 | 3160 | 65896 | 20853 |

TABLE 5B

| Time (h) | $C_{prot.}$ (µg/ml) | Activity (+fibrin) (U/ml) | Activity/$C_{prot.}$ (U/mg) |
|---|---|---|---|
| 1 mol/l Tris, $C_{prot.}$ = 31 µg/ml per 30 min. | | | |
| 1 | 94 | 1590 | 16914 |
| 3 | 218 | 6265 | 28738 |
| 18 | 1094 | 33897 | 30984 |
| 42 | 2563 | — | — |
| 49 | 3031 | 53033 | 17496 |
| 65 | 3696 | 72056 | 19495 |
| without Tris, $C_{prot.}$ = 31 µg/ml per 30 min. | | | |
| 1 | 94 | 107 | — |
| 3 | 219 | 4587 | 20945 |
| 18 | 1094 | 20257 | 18516 |
| 42 | 2563 | 23580 | 9200 |
| 49 | 3031 | 33482 | 11046 |
| 65 | 3936 | 36126 | 9774 |

An approximation to a continuous process (increasing the rate of addition of the individual renaturation pulses under conditions which are otherwise equivalent) yields the same renaturation rates in comparison to the pulse experiment. The addition of 1 mol/l Tris to the renaturation buffer in general increases the final yield by ca. 20% to 100%.

EXAMPLE 6

Dependence of the renaturation of reduced K2P on the Tris concentration

Starting material: Inclusion bodies (IB's) of the tPA mutein K2P, produced according to Example 1.

| Solubilization: | 6 mol/l Gdn/HCl, pH 8.3 |
|---|---|
| | 0.1 mol/l Tris |
| | 1 mmol/l EDTA |
| | 0.1 mol/DTE |
| | $C_{prot.}$ = 7.5 mg/ml |
| | 2 min Ultraturrax |
| | incubation: 1 h at room temperature |
| | stopping: pH 3.0 with HCl |
| Dialysis: | 6 mol/l Gdn/HCl, pH 3.0 |
| | 1 mmol/l EDTA |
| Renaturation: | 0.7 mol/l Arg/HCl, pH 8.5 |
| | 1 mmol/l EDTA |
| | 3 mmol/l GSH |
| | 0.3 mmol/l GSSG (oxidized glutathione) |
| | Tris: 0; 0.3; 0.6; 0.9; 1.2; 1.5; 1.8 and 2.1 mol/l |
| | $C_{prot.}$ = 150 µg/ml |

The result can be seen in Table 6.

TABLE 6

| Tris (mol/l) | Activity (U/ml) |
|---|---|
| 0 | 1339 |
| 0.3 | 1478 |
| 0.6 | 1591 |
| 0.9 | 1725 |
| 1.2 | 1766 |
| 1.5 | 1766 |
| 1.8 | 1725 |
| 2.1 | 1717 |

Even when the reduced protein is directly renatured the renaturation yield is increased by 30% by the addition of $\geq 1$ mol/l Tris.

EXAMPLE 7

Renaturation of G-CSF

Starting Material:

Inclusion bodies of G-CSF, produced according to PCT/EP91/00192 (Example 3)

| Solubilization: | 6 mol/l Gdn/HCl, pH 8 |
|---|---|
| | 0.1 mol/l Tris |
| | 1 mmol/l EDTA |
| | 0.1 mol/l DTE |
| | $C_{prot.}$ = 10 mg/ml |
| | 2 min Ultraturrax |
| | incubation: 2 h at room temperature while stirring |
| | stopping: pH 3 with HCl |
| Dialysis: | 6 mol/l Gdn/HCl, pH 2.5 |
| | 3 mmol/l EDTA |
| | 4° C., until the reducing agent is completely removed |
| Protein concentration after dialysis: 8.5 mg/ml | |
| Renaturation: | |

Experiment I:

0.6 mol/l Arg/HCl, pH 8
1 mmol/l EDTA
0.5 mmol/l GSH
5 mmol/l GSSG

-continued

| | |
|---|---|
| A) | 0.1 mol/l Tris |
| B) | 1 mol/l Tris |
| | pulse: |
| | C = 50 µg/ml in 30 min |
| | t = 1 h |
| | final protein conc. = 1 mg/ml |
| | Experiment II: |
| | 0.6 mol/l Arg/HCl, pH 8 |
| | 1 mmol/l EDTA |
| | 0.5 mmol/l GSH |
| | 5 mmol/l GSSG |
| A) | 0.1 mol/l Tris |
| B) | 1 mol/l Tris |
| | pulse: |
| | C = 50 µg/ml in 30 min |
| | t = 1 h |
| | protein concentration = 0.6 mg/ml |

After the renaturation a centrifugation is carried out at 16000 rpm, 30 min. Subsequently a dialysis is carried out against 20 mmol/l Tris, pH 8, 1 mmol/l EDTA.

The result can be seen in Table 7.

TABLE 7

| Experiment | % renaturation after dialysis in Tris buffer pH 8.0 |
|---|---|
| Experiment I | |
| A: 0.1 mol/l Tris | 10 |
| B: 1 mol/l Tris | 63 |
| Experiment II | |
| A: 0.1 mol/l Tris | 20 |
| B: 1 mol/l Tris | 50 |

The determination of the activity of G-CSF is carried out with the aid of a proliferation test ($^3$H-thymidine incorporation) using a G-CSF-dependent murine leukemia cell line (NFS60) as described in Mossmann, T. (1985) J. Immunol. Methods 65, 66–73 and Holmes, K. L.; Plaszynski, E.; Frederickson, T. T.; Morse, H. C. III & Ihle, J. (1985) PNAS USA 82, 6687–6691. Analogous results are obtained with G-CSF and G-CSF muteins produced according to EP 91 107 429.2.

EXAMPLE 8

Renaturation of Antibody Fab Fragments

| | |
|---|---|
| Denaturation: | 5 mol/l Gdn/HCl, pH 8.5 |
| | 0.1 mol/l Tris |
| | 2 mmol/l EDTA |
| | 0.3 mol/l DTE |
| | $C_{prot.}$ = 5 mg/ml |
| | incubation: 2–3 h at room temperature |
| Renaturation: | Tris buffer, pH 7.5 |
| | (Tris: 0.05; 0.1; 0.2; 0.3; 0.5; 0.75 and 1 mol/l) |
| | 2 mmol/l EDTA |
| | 6 mmol/l GSSG |
| | $C_{prot.}$ = 50 µg/ml |
| | incubation: 80 h at 10° C. |
| Activity test: | ELISA with biotinylated CK according to DE-A 38 35 350.4 (Example 8.2). |

The result can be seen in Table 8.

TABLE 8

| Tris (mol/l) | % Renaturation |
|---|---|
| 0.05 | 13 |
| 0.1 | 18 |
| 0.2 | 22 |
| 0.3 | 27 |
| 0.5 | 35 |
| 0.75 | 36 |
| 1 | 37 |

There is a linear increase in the renaturation yield of the antibody Fab's up to a Tris concentration of 0.5 mol/l; a further increase in the Tris concentration only leads to a slight improvement.

We claim:

1. Process for reactivating a denatured protein comprising incubating said denatured protein with a solution of Tris base or a salt of Tris at a concentration of at least 400 mmol/l and at a pH at which said denatured protein can take up its native conformation, for a time sufficient to reactivate said denatured protein.

2. The process of claim 1, comprising adjusting the pH value of the solution in which said denatured protein is incubated by adding a buffer substance which is different from Tris.

3. The process of claim 1, comprising adjusting the pH value of said solution in which said denatured protein is incubated by adding Tris thereto.

4. The process of claim 1, wherein said Tris solution is at a concentration of from 0.4 to 2 mol/l.

5. The process of claim 1 further comprising adding from 0.2 to 1.0 mol/l arginine to said solution.

6. The process of claim 5, wherein said denatured protein is recombinant tPA or a tPA mutein.

7. The process of claim 6 wherein said tPA mutein is non-glycosylated and has domain composition K2P.

8. The process of claim 1 comprising adding said denatured protein continuously or batchwise to said solution.

9. The process of claim 8 wherein said process is carried out via pulse renaturation in a renaturation reactor.

10. The process of claim 9, comprising carrying out said renaturation in a buffer containing arginine, and a Tris concentration of about 1 mol/l, and said denatured protein is added in increments of about 200 ug per pulse.

11. The process of claim 1, wherein said denatured protein is recombinant G-CSF.

12. The process of claim 1, wherein said denatured protein is an antibody or an antibody fragment.

* * * * *